United States Patent
Säll

(10) Patent No.: US 10,159,800 B2
(45) Date of Patent: Dec. 25, 2018

(54) MEDICAMENT DELIVERY DEVICE WITH DELIVERY FINISH SIGNAL DELAY

(71) Applicant: CAREBAY EUROPE LTD., Sliema (MT)

(72) Inventor: Daniel Säll, Segeltorp (SE)

(73) Assignee: CAREBAY EUROPE LTD, Sliema (MT)

( * ) Notice: Subject to any disclaimer, the term of this patent is extended or adjusted under 35 U.S.C. 154(b) by 208 days.

(21) Appl. No.: 15/116,149

(22) PCT Filed: Jan. 30, 2015

(86) PCT No.: PCT/EP2015/051892
§ 371 (c)(1),
(2) Date: Aug. 2, 2016

(87) PCT Pub. No.: WO2015/121081
PCT Pub. Date: Aug. 20, 2015

(65) Prior Publication Data
US 2017/0165428 A1 Jun. 15, 2017

(30) Foreign Application Priority Data
Feb. 17, 2014 (SE) ...................................... 1450183

(51) Int. Cl.
*A61M 5/315* (2006.01)
*A61M 5/20* (2006.01)
(Continued)

(52) U.S. Cl.
CPC ........ *A61M 5/3157* (2013.01); *A61M 5/2033* (2013.01); *A61M 5/321* (2013.01);
(Continued)

(58) Field of Classification Search
CPC .... A61M 5/3157; A61M 5/2033; A61M 5/20; A61M 5/3202; A61M 5/3243;
(Continued)

(56) References Cited

U.S. PATENT DOCUMENTS

| 2010/0049125 A1* | 2/2010 | James ................. A61M 5/2033 604/110 |
| 2013/0204183 A1* | 8/2013 | Noderer .............. A61M 5/3135 604/68 |

FOREIGN PATENT DOCUMENTS

| EP | 2583705 | 4/2013 |
| WO | 2011/043714 | 4/2011 |

(Continued)

OTHER PUBLICATIONS

International Search Report and Written Opinion for Int. App. No. PCT/EP2015/051892, dated May 6, 2015.

(Continued)

*Primary Examiner* — Bhisma Mehta
*Assistant Examiner* — James D Ponton
(74) *Attorney, Agent, or Firm* — McDonnell Boehnen Hulbert & Berghoff LLP

(57) ABSTRACT

A medicament delivery device is present having a housing with a distal and a proximal end, the housing being adapted to receive a medicament container with a delivery member or with a connectable delivery member for delivery of a medicament. A drive mechanism acts on the medicament container to deliver the medicament. An actuator is interactively connected to the drive mechanism for holding the drive mechanism in a pre-tensioned state. A biased delivery member cover is positioned at least partially and axially movable within the housing and is interactively connected to the actuator, such that when the biased delivery member cover is pressed against a delivery site the actuator releases the drive mechanism from the pre-tensioned state. A signal delay mechanism is operably connected to said drive mechanism to generate an audible and/or tactile and/or visual signal indicating that the medicament has been completely delivered.

17 Claims, 9 Drawing Sheets

(51) Int. Cl.
*A61M 5/32* (2006.01)
*A61M 5/31* (2006.01)
(52) U.S. Cl.
CPC ........ *A61M 5/3202* (2013.01); *A61M 5/3204* (2013.01); *A61M 5/3243* (2013.01); *A61M 2005/208* (2013.01); *A61M 2005/2013* (2013.01); *A61M 2005/3143* (2013.01); *A61M 2005/3247* (2013.01); *A61M 2205/581* (2013.01); *A61M 2205/582* (2013.01); *A61M 2205/583* (2013.01)
(58) Field of Classification Search
CPC .. A61M 5/3257; A61M 5/326; A61M 5/3271; A61M 2005/2026; A61M 2005/3261; A61M 2005/3267; A61M 2005/3268; A61M 2005/2013; A61M 2005/208; A61M 2005/3143; A61M 2205/581; A61M 2205/582; A61M 2205/583
See application file for complete search history.

(56) References Cited

FOREIGN PATENT DOCUMENTS

| | | |
|---|---|---|
| WO | 2011/109205 | 9/2011 |
| WO | 2013/178512 | 12/2013 |

\* cited by examiner

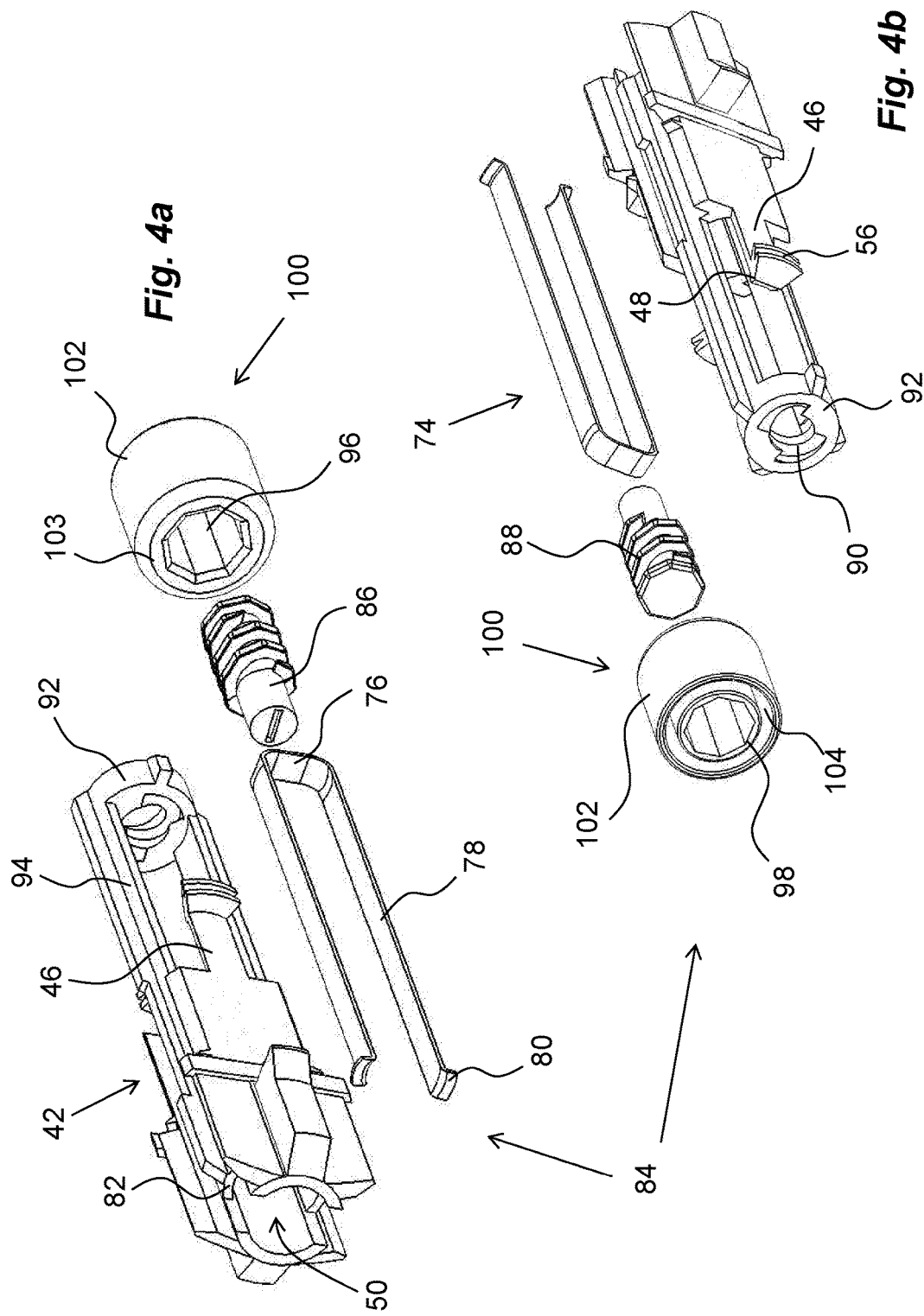

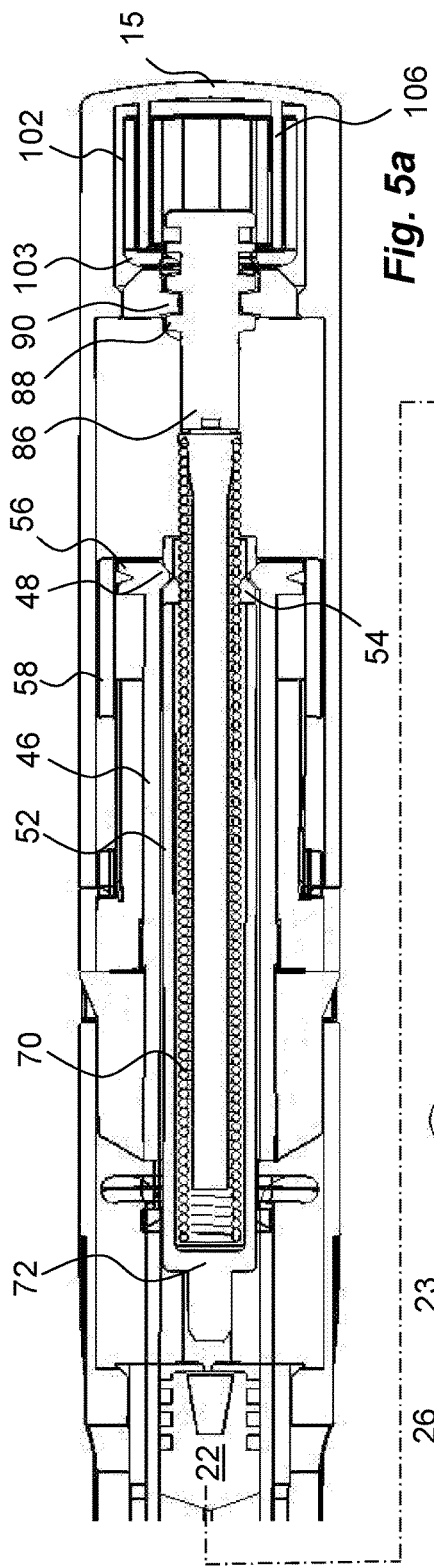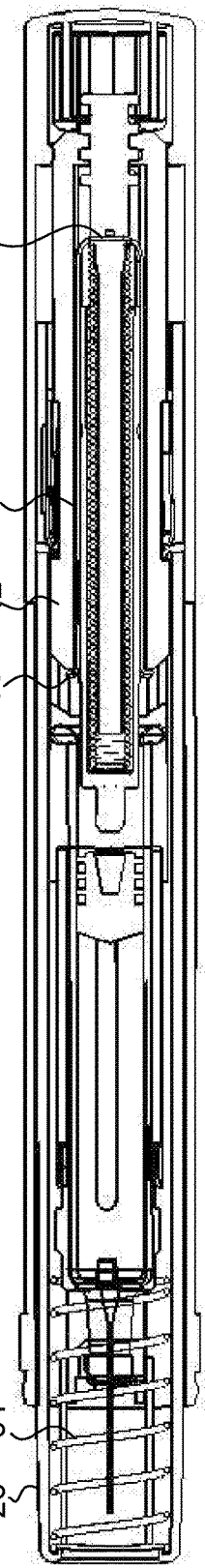
Fig. 5a
Fig. 5b

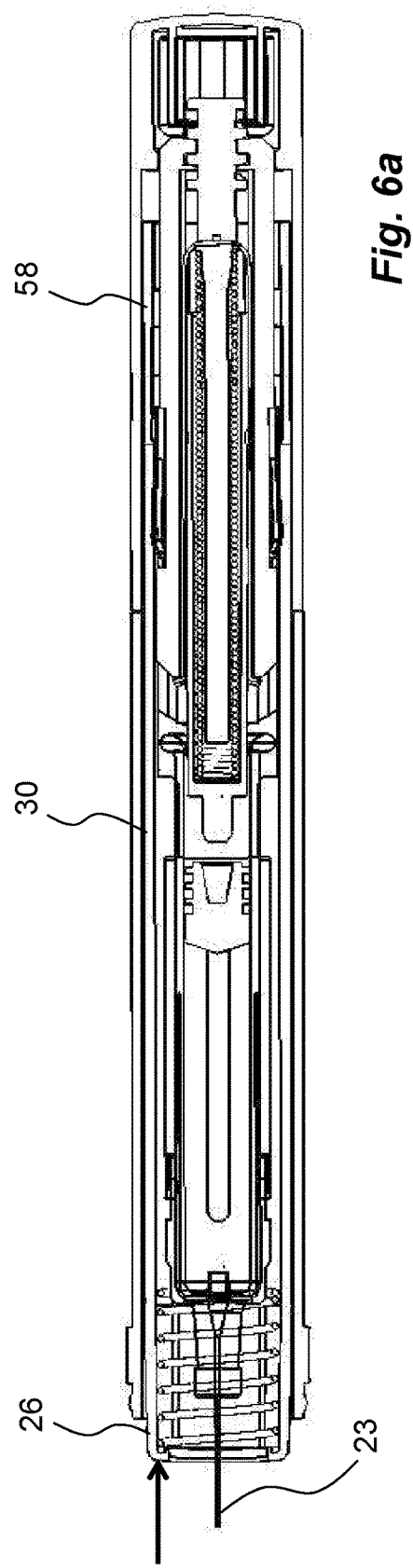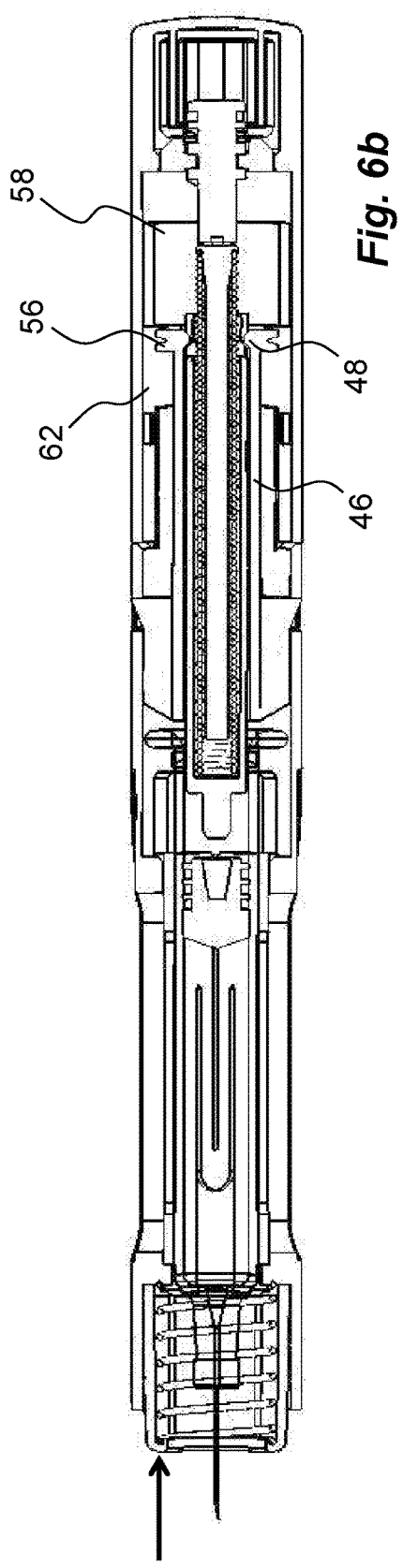

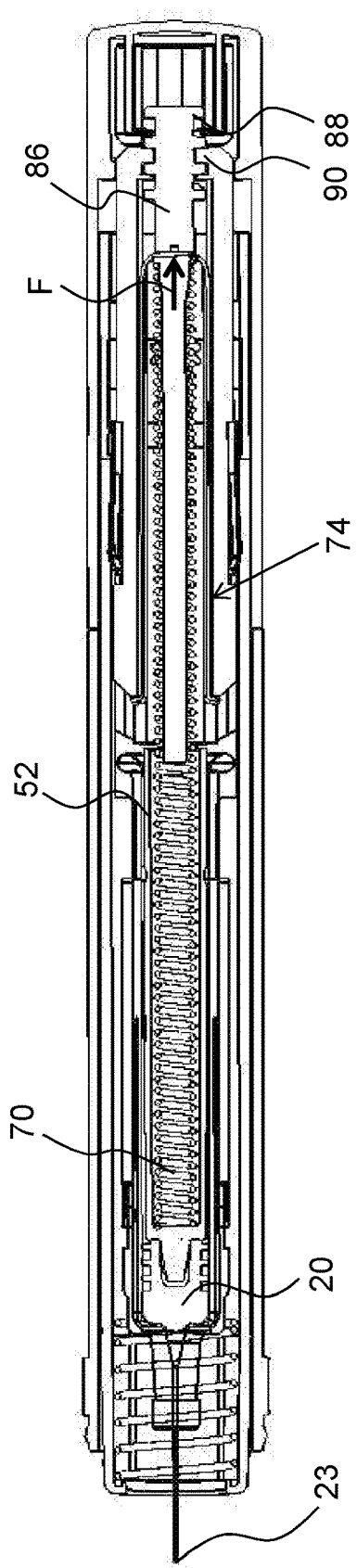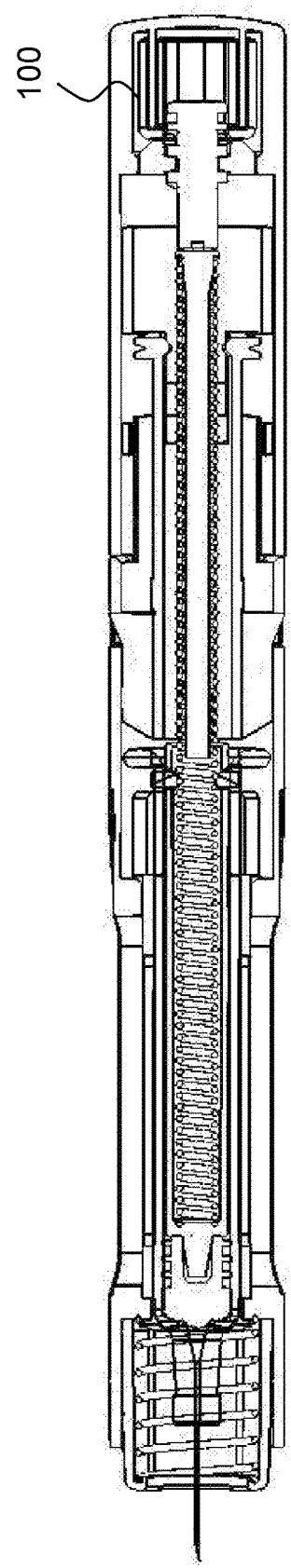
*Fig. 7a*
*Fig. 7b*

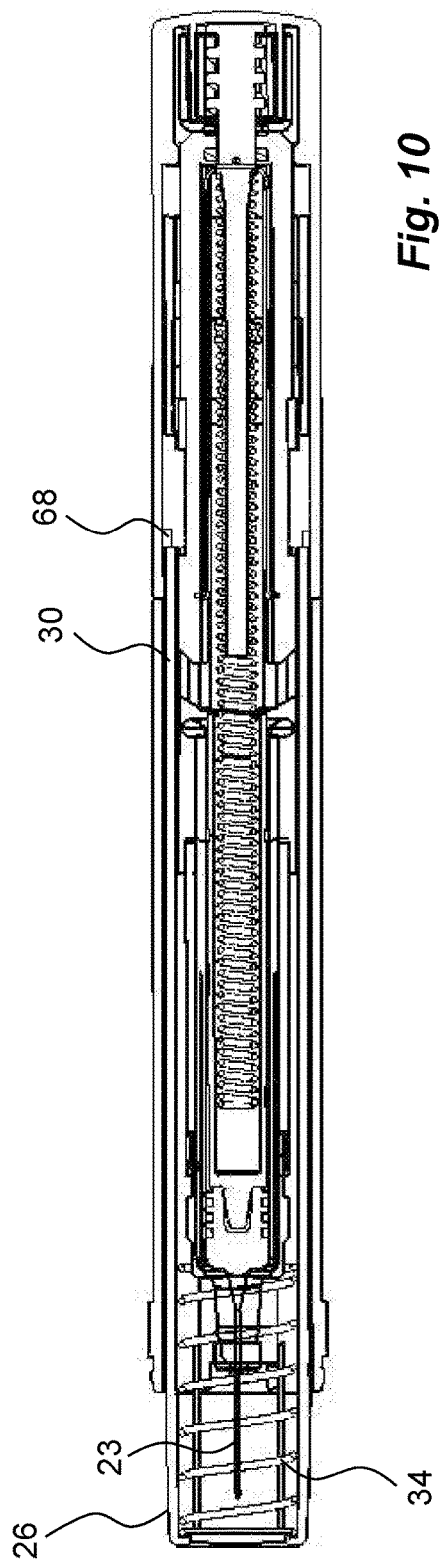
Fig. 10
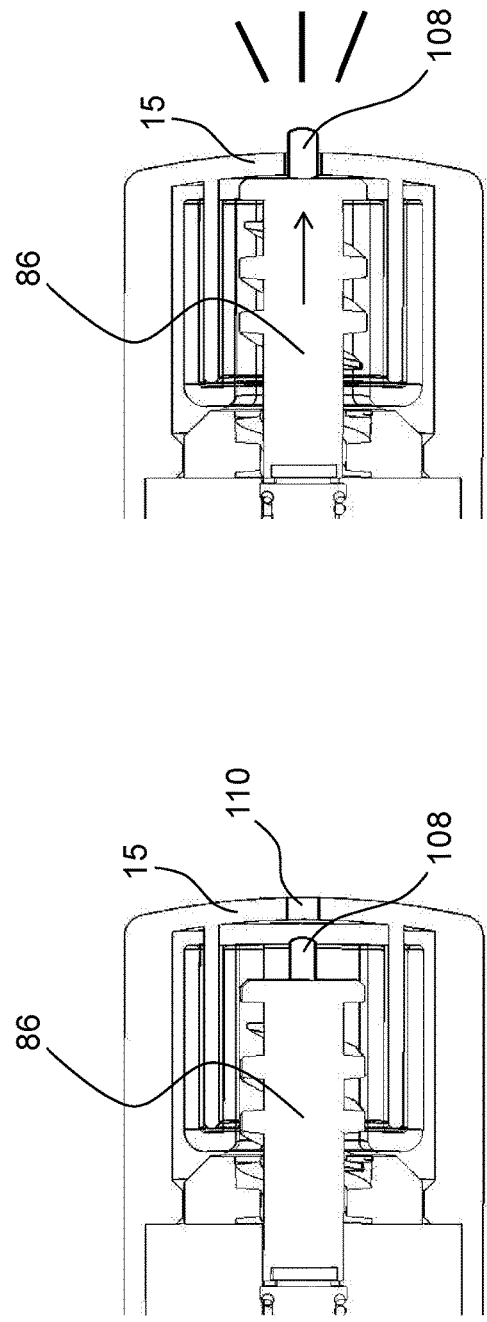
Fig. 11b
Fig. 11a

MEDICAMENT DELIVERY DEVICE WITH DELIVERY FINISH SIGNAL DELAY

CROSS REFERENCE TO RELATED APPLICATIONS

The present application is a U.S. National Phase Application pursuant to 35 U.S.C. § 371 of International Application No. PCT/EP2015/051892 filed Jan. 30, 2015, which claims priority to Swedish Patent Application No. 1450183-7 filed Feb. 17, 2014. The entire disclosure contents of these applications are herewith incorporated by reference into the present application.

TECHNICAL FIELD

The present invention relates to a medicament delivery device and in particular a device capable of indicating to a user when a medicament delivery sequence has been completed such that it is safe to remove the device from the dose delivery site.

BACKGROUND

Many medicament delivery devices are developed for self-administration, i.e. a user performs the medicament delivery her-, or himself. This requires a medicament delivery device which is reliable, accurate, safe and easy to use. In order to meet these requirements, the risk of human errors must be minimized, the number of actions needed to be performed in order to receive a dose need to be reduced and the device must be intuitive to use. Thus, in order to minimize the risk of human errors, it is desirable to have a device that accurately provides a user with confirmation that he/she has received a complete dose of medicament.

Medicament delivery devices such as injection devices providing automatic or manual delivery member insertion, automatic injection of a medicament, automatic delivery member retraction or automatic covering of the delivery member are known in the art. Though these injection devices known in the art have a major number of advantages, there is always room for improvement. For example, a device that provides both a complete delivery of medicament and release of a member that produces a reliable audible and/or tactile and/or visible confirmation to the user that the delivery has been completed has hitherto been required to be manufactured to extremely tight tolerances.

For example, a release of a member that produces a reliable audible and/or tactile and/or visible confirmation to the user that the delivery has been completed is disclosed in WO2011/043714A1. The release of a member that produces a reliable audible and/or tactile and/or visible confirmation to the user that the delivery has been completed is accomplished by disengaging a plunger rod from a second activator member once the plunger rod has terminated its displacement for delivering the medicament. The termination of the plunger rod displacement and the disengaging of the plunger rod from the second activator member must occur simultaneously if both a complete delivery of a medicament and a release of the second activator member which produces the reliable audible and/or tactile and/or visible confirmation to the user that the delivery has been completed are to be accomplished.

Thus, in WO2011/043714A1 there is only one mechanical position that is used to activate the release of the second activation member at the point where it is expected that the plunger displacement will terminate. The precision of the timing of the termination of plunger displacement and disengagement of the plunger from the second activation member relies on the manufacturing and assembly dimensions of the parts of the device and thus the tolerances play an important role in the proper functioning of the device.

Thus, in order to compensate for component tolerances a signal generating member needs to be released before the plunger displacement has terminated. A user may then be prone to remove the device from the delivery site causing the medicament to not be completely delivery to the patient. In order to ensure a complete and accurate delivery of a medicament all the parts or components of the device must be manufactured to very tight tolerances leading to high manufacturing and assembling costs. Even the medicament container must be manufactured with such tight tolerances in mind, which is rare.

Thus, it would be an improvement in the art to provide a medicament delivery device that can be manufactured and assembled having reliable effects such as a complete delivery of a medicament followed by an audible and/or tactile and/or visible confirmation to the user that the delivery has been completed.

SUMMARY

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient. Further, when the term "distally" is used, this refers that a part/member/element of the device is moved/to be moved towards the end that is located furthest away from the medicament delivery site of the patient. Correspondingly, when the term "proximally" is used, this refers that a part/member/element of the device is moved/to be moved towards the end that is located closest to the medicament delivery site of the patient.

The aim of the present invention is to remedy the drawbacks of the state of the art medicament delivery devices. This aim is obtained by a medicament delivery device comprising the features of the independent patent claim 1. Preferable embodiments of the invention form the subject of the dependent patent claims.

According to the medicament delivery device described herein, it comprises a housing having a distal and a proximal end. The housing may have one or several housing parts depending on the actual configuration and design, wherein the housing parts, if more than one, may be arranged with suitable fastening mechanisms, either for permanent attachment or for releasable connection.

The housing may preferably be adapted to receive a medicament container with a delivery member. The delivery member may either be an integrated part of the medicament container or may be arranged with suitable connection mechanism for connecting a suitable delivery member for delivery of a medicament. If the medicament delivery member is connectable, then a number of suitable connection elements may be used such as e.g. threads, bayonet connections, luer connections etc.

The medicament delivery device may further preferably be arranged with a drive mechanism arranged to act on the medicament container for providing automatic delivery of the medicament. The drive mechanism may be provided with suitable force elements such as springs. Then different types of springs may be utilized that are capable of performing a dose delivery sequence. There are many types of springs that can be used such as compression springs, clock springs, torsion springs, volute springs, gas springs just to mention a few. The drive mechanism may be configured to be actuated from a pre-tensioned state to a released state.

The device may further comprise a biased delivery member cover positioned at least partially and axially movable within the housing, said biased delivery member cover being interactively connected to the drive mechanism such that when said biased delivery member cover is pressed against a delivery site said drive mechanism is actuated whereby the drive mechanism acts on the medicament container for providing automatic delivery of the medicament The device may further comprise a signal delay mechanism operably connected to said drive mechanism for generating an audible and/or tactile and/or visual signal indicating that the medicament has been completely delivered.

According to a preferable solution, the signal delay mechanism comprises an activator interactively arranged to said drive mechanism, a signal generating element interactively connected to the activator and to an actuator of the drive mechanism, and a delay element operably connected to the housing and to the signal generating element for delaying said generation of an audible and/or tactile and/or visual signal.

The signal generating element then is capable of positively indicating to the user that it is safe to remove the device from the dose delivery site. The signal delay mechanism ensures that the medicament container is completely emptied before the user receives an indication that it is safe to remove the device. The delay mechanism thus delays the signal for a certain time period, thereby minimizing the risk that the device is prematurely removed.

According to a possible solution, the signal generating element is arranged movable in a longitudinal direction in relation to the actuator. Preferably, the delay element is rotatably connected to the housing and is placed in contact with a viscous media capable of regulating the rotational speed of said delay element when the signal generating element acts on the delay element. Further, the signal generating element and the delay element are rotationally locked to each other while admitting longitudinal movement between them. With this solution, the rotational speed of the delay element is controlled by the properties of the viscous media. The solution provides a controlled delay movement with few components, thereby providing a reliable and stable delay mechanism. According to a preferable solution, the viscous media may be damping grease. Damping grease as such has been used in many technical fields e.g. for reducing play between components, or to give a certain resistance to turnable components which provides a user with a feeling of quality and precision. Thus damping grease has a number of advantages when it comes to controlling movement of movable and turnable elements.

According to a feasible solution, the signal generating element is arranged with threads configured to cooperate with corresponding fixed threads on said actuator such that said signal generating element and said delay element rotate when said activator is activated. The threads then provided a rotational movement of the signal generating element as well as the delay element and at the same time the signal generating element is moved in the longitudinal direction by the threads in order to position it such that it provides the signal that it is safe to remove the device.

In this aspect, the threads on said signal generating element terminate at a certain release point of said signal generating element whereby said signal generating element is released from the actuator and wherein a certain distance is provided between a distal transversal surface of the signal generating element and an inner transversal surface on the housing at said release point such that said signal generating element is free to be moved in contact with said inner transversal surface, thereby generating said audible and/or tactile and/or visual signal. The release of the signal generating element thus causes it to be forced to hit the inner transversal surface on the housing, where the impact will cause a sound as well as a tactile indication.

As a another development, the signal generating element comprises a protrusion extending in a distal direction, and wherein said inner transversal surface on the housing comprises a passage, wherein said protrusion is arranged to extend through said passage for generating a tactile and a visual signal. With this solution both an audible, tactile as well as visual indication is obtained. For example the protrusion may be of a bright and/or specific colour which clearly indicates to the user that the device may be removed.

According to a preferable solution the delay is a generally tubular body comprising a generally cylindrical hub, wherein an annular compartment is created between said hub and said generally tubular body, and wherein the housing comprises a generally tubular protrusion arranged in said compartment and wherein the viscous media is arranged in said compartment. Preferably, the viscous media comprises a damping grease. The viscous media in the compartment will thus control the rotational speed of the delay element due to its properties.

As a further development, the activator is a U-shaped bracket having a base and two arms, wherein the free ends of the arms are arranged with generally radially outwardly directed ledges, and wherein the base is in contact with said signal generating element.

Furthermore, the drive mechanism comprises a generally tubular plunger rod partially arranged within a central passage of the actuator and in contact with the arms of the U-shaped bracket such that the ledges are arranged to be in contact with a proximally directed surface surrounding the central passage of the actuator, and a compression spring placed inside a cavity of the plunger rod with a proximal end thereof in contact with an end wall of the plunger rod and a distal end thereof in contact with the base of the U-shaped bracket. The actuator comprises longitudinally extending grooves on which distally directed end surfaces of elongated arms of the biased delivery member cover may slide, and radially flexible and distally directed arms having radially inwardly directed protrusions and outwardly directed protrusions at the free ends and wherein the radially inwardly directed protrusions are configured to fit into cut-outs of the plunger rod.

The drive mechanism further comprises a generally tubularly shaped actuator lock sleeve coaxially and slidably arranged on the actuator and wherein the actuator lock sleeve is further arranged with cut-outs or windows. The drive mechanism is in a pre-tensioned state when the plunger rod is held in position in relation to the actuator by the protrusions of the arms placed in the cut-outs of the plunger rod such that the compression spring is held tensioned between the end wall of the plunger rod and the base of the activator, wherein the arms are prevented from being moved outwardly in the radial direction by the actuator lock sleeve which is positioned radially outside the arms such that the outwardly directed protrusions of the arms are in contact with an inner surface of the actuator lock sleeve and wherein the ledges of the activator are resting on the surface of the actuator such that the activator is prevented from being moved in the distal direction by the force of the spring. The drive mechanism is in a released state when the biased delivery member cover and thereby the actuator lock sleeve are moved longitudinally towards the distal end such that the windows of the actuator lock are placed radially outside the outwardly directed protrusions of the arms of the actuator allowing the arms to flex radially outwards and thereby disengaging from the cut-outs of the plunger rod.

As a further development, the arms of the activator are configured to flex radially inwards such that the ledges are moved out of contact with the surfaces of the actuator when the plunger rod has moved proximally a certain distance and is moved out of contact with the arms.

According to one possible solution, the activator is configured to be distally moved by the compression spring when the plunger rod has moved proximally a certain distance and is moved out of contact with the arms such that the activator presses with a distally directed force F on the signal generating element. Furthermore, the signal generating element and the delay element are configured to rotate when the activator presses with the distally directed force F on the signal generating element.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION

Figure 1:
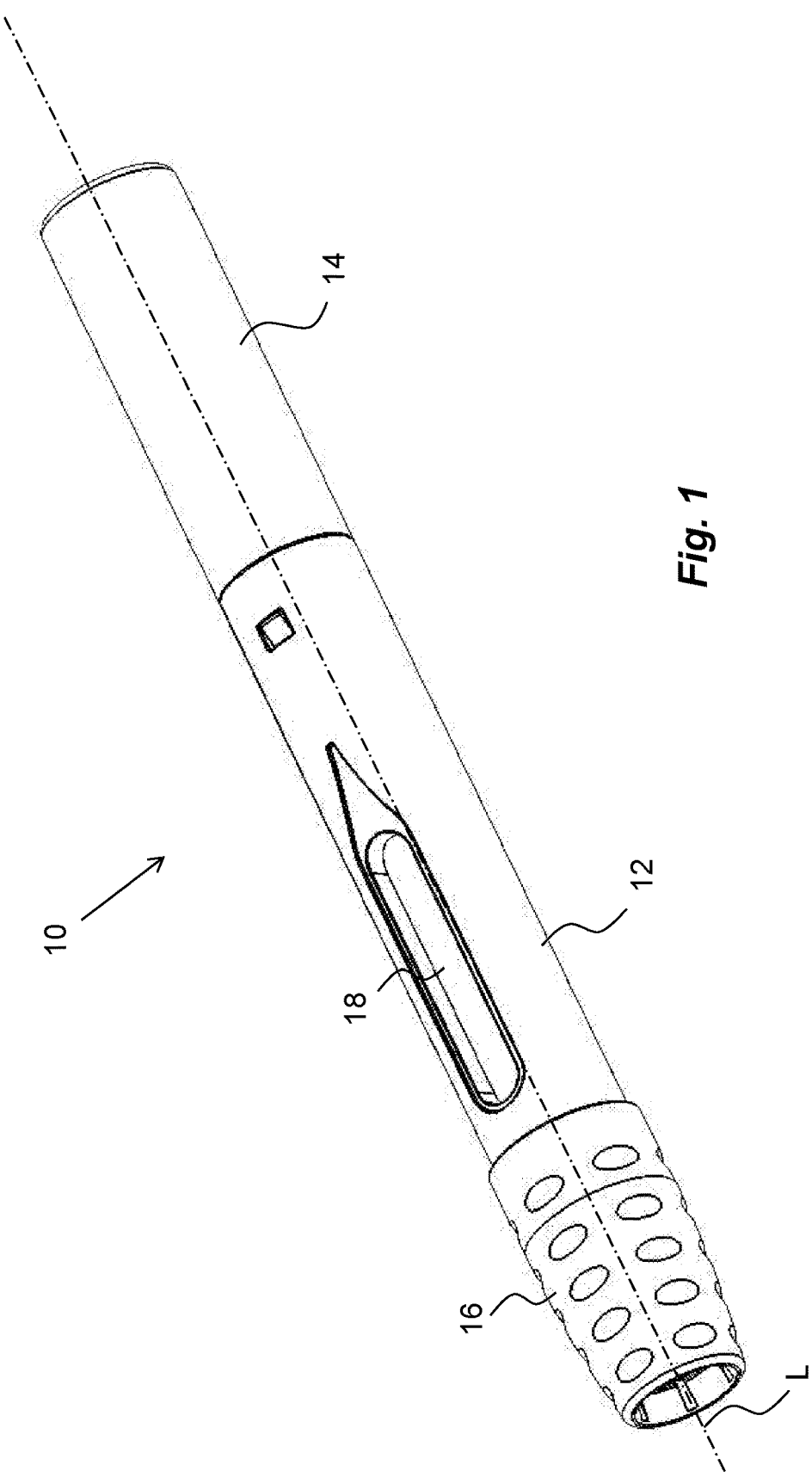
FIG. 1 is a perspective view of a an embodiment of a medicament delivery device according to the invention.

The embodiment of a medicament delivery device 10 shown in the drawings comprises a housing having a generally tubular proximal housing part 12 and a generally tubular distal housing part 14, FIG. 1. Suitable attachment elements are arranged on the housing parts for interconnection. The attachment elements may comprise mechanical fasteners like threads, snap-in tongues or the attachment elements may comprise gluing or welding of the housing parts. The distal housing part 12 is further arranged with a distal end wall 15. The device 10 is also arranged with a protective cap 16, FIG. 1. The proximal housing part 12 is further arranged with openings or windows 18, FIG. 1, through which a medicament container 20 is visible, FIG. 2. The medicament container 20 is preferably made of a transparent material, such as suitable plastic or glass so that the medicament is visible. A stopper 22 is arranged inside the medicament container 20 and movable in the longitudinal direction L.

A medicament delivery member 23 is further arranged to the medicament container. In the embodiment shown, the delivery member 23 is an injection needle, but it is to be understood that other types of delivery members may be used, such as nozzles, mouthpieces, nebulizers etc. Also, the medicament delivery member 23 shown in the embodiment is integrated with the medicament container as one piece. It is however to be understood that the medicament delivery member 23 may be arranged as a separate element that is attachable, fixedly or removably, to the medicament container 20 by appropriate fastening elements such as threads, bayonet couplings, luer connections, etc.

The medicament container 20 is arranged to be housed in the housing, more particularly in the proximal housing part 12 by a medicament container holder 24 arranged as a generally tubular body having a diameter smaller than the inner diameter of the proximal housing part 12, creating an annular gap between the two. The medicament container holder 24 is arranged with suitable attachment elements interconnecting with the proximal housing part 12. Further a biased delivery member cover 26, in the embodiment shown in the form of a needle shield is arranged inside the proximal housing part 12 and movable in the longitudinal direction in relation to said housing.

The biased delivery member cover 26 is arranged with a proximal generally tubular part 28. Two elongated arms 30 are attached to the proximal part and extending in the distal direction in the gap between the proximal housing part 12 and the medicament container holder 24. The elongated arms 30 terminate in distally directed end surfaces 32, FIG. 2. A biased delivery member cover spring 34 is arranged between a distally directed annular ledge 36 on the biased delivery member cover 26 and a proximally directed annular ledge 38 on the inner surface of the proximal housing part 12, FIG. 5a.

Figure 2:
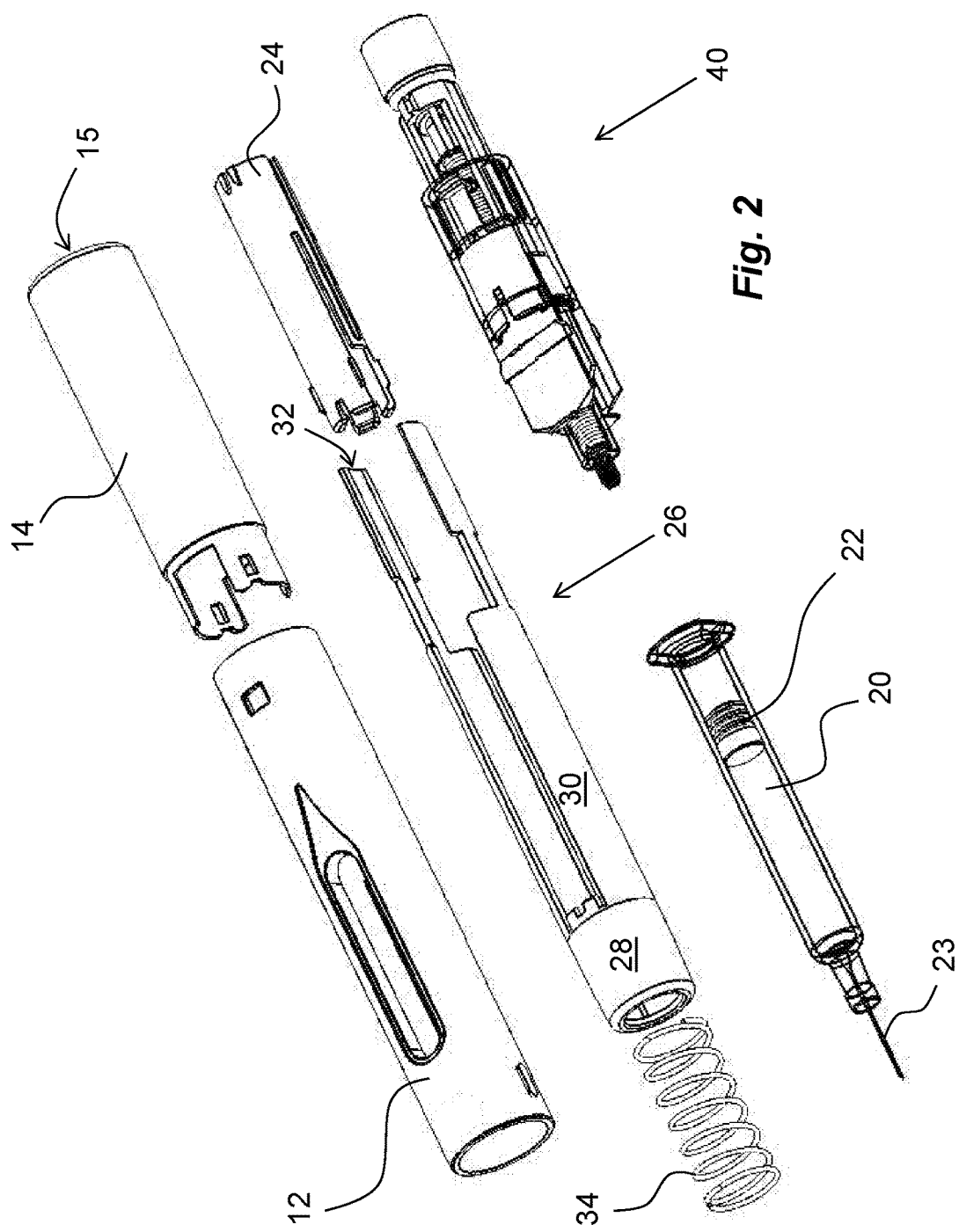
FIG. 2 is an exploded view of the embodiment of FIG. 1, FIGS. 3 and 4 are detailed views of components comprised in the embodiment of FIG. 1, FIGS. 5-10 are cross-sectional views showing different functional positions of the embodiment of FIG. 1, and FIGS. 11a, b are cross-sectional views showing a variant of a signal generating element comprised in the present invention.
Figure 3:
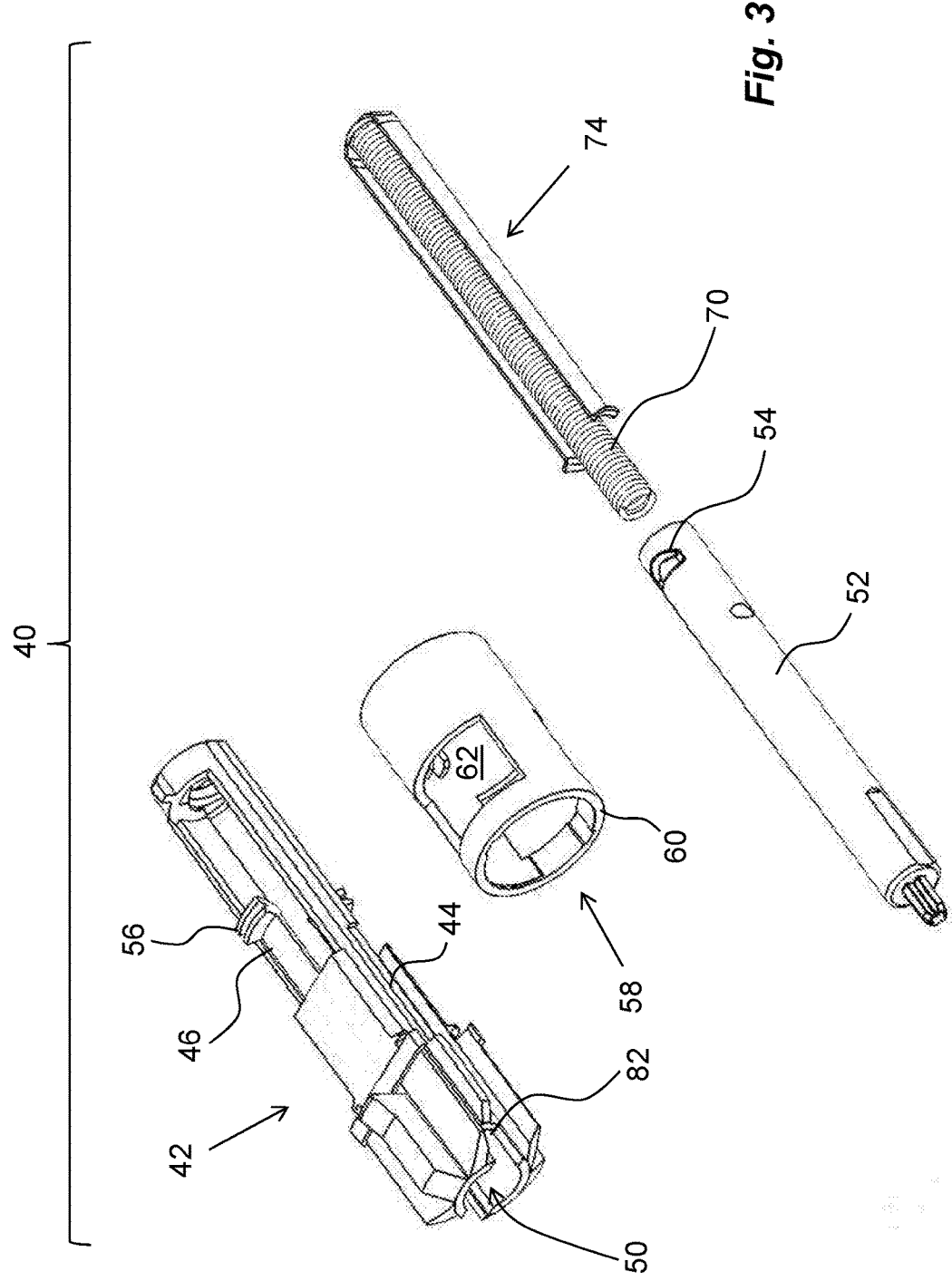
Figure 9:
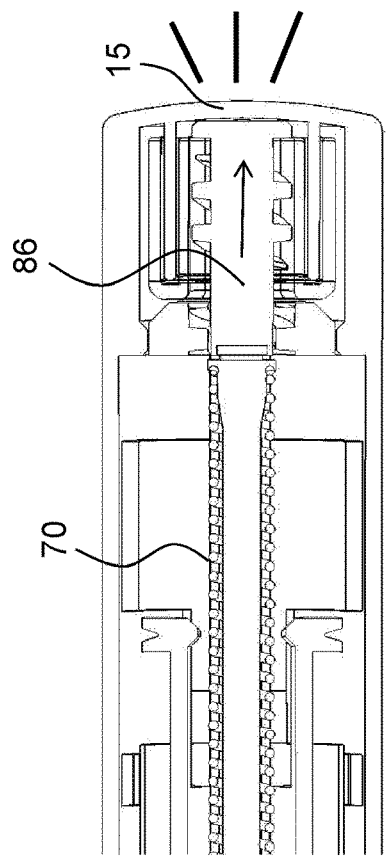

The medicament delivery device further comprises a drive mechanism 40, FIGS. 2 and 3, configured to be actuated from a pre-tensioned state to a released state. The biased delivery member cover 26 is interactively connected to the drive mechanism 40 such that when said biased delivery member cover 26 is pressed against a delivery site the drive mechanism 40 is actuated whereby the drive mechanism acts on the medicament container 20 for providing automatic delivery of the medicament The drive mechanism 40 comprises an actuator 42 having a generally elongated body. Longitudinally extending grooves 44 are arranged on the outer surface of the actuator 42, in which grooves 44 the elongated arms 30 of the biased delivery member cover 26 may slide in the longitudinal direction L as will be described below. The body of the actuator 42 further comprises distally directed arms 46, which arms 46 are arranged flexible in directions generally perpendicular to the longitudinal direction L. The free ends of the arms 46 are arranged with radially inwardly directed protrusions 48, FIGS. 4b and 5a.

The device also comprises a signal delay mechanism 84 operably connected to said drive mechanism 40 for generating an audible and/or tactile and/or visual signal indicating that the medicament has been completely delivered. The signal delay mechanism 84 comprises an activator 74 interactively arranged to said drive mechanism, a signal generating element 86 interactively connected to the activator 74 and to the actuator 42 of the drive mechanism, and a delay element 100 operably connected to the housing and to the signal generating element 86 for delaying said generation of an audible and/or tactile and/or visual signal. The signal generating element 86 is arranged movable in a longitudinal direction in relation to the actuator 42.

The drive mechanism further comprises a generally tubular plunger rod 52. The actuator 42 is further arranged with a central passage 50 through which the generally elongated plunger rod 52 may extend, FIG. 3. The plunger rod 52 is arranged with cut-outs 54, in which cut-outs 54 the protrusions 48 of the actuator may fit as seen in FIG. 5*a*. The free ends of the arms 46 of the actuator 42 are further arranged with outwardly directed protrusions 56, FIGS. 4*b* and 5*a*.

The drive mechanism also comprises a generally tubularly shaped actuator lock sleeve 58 coaxially and slidably arranged on the actuator 42. The protrusions 56 are arranged to interact with the generally tubularly shaped actuator lock sleeve 58, FIGS. 3 and 5*a*. The actuator lock sleeve 58 is arranged slidable along the longitudinal direction L and is positioned such that a proximal end surface 60 thereof is in contact with the distally directed end surfaces 32 of the elongated arms 30 of the biased delivery member cover 26. The actuator lock sleeve 58 is further arranged with cut-outs or windows 62, FIG. 3.

The delay element 100 is rotatably connected to the housing and is placed in contact with a viscous media capable of regulating the rotational speed of said delay element 100 when the signal generating element acts on the delay element. Further, the signal generating element 86 and the delay element 100 are rotationally locked to each other while admitting longitudinal movement between them, as it will be explained below. The delay element 100 is preferably a generally tubular body 102 comprising a generally cylindrical hub 98, wherein an annular compartment 104 is created between said hub 98 and said generally tubular body 102 as seen in FIG. 4*b*.

The inner proximally directed surface of the end wall 15 of the distal housing part 14 is arranged with a tubular protrusion 106, FIG. 5*a*, wherein the delay element 100 and the tubular protrusion 106 are positioned such that the tubular protrusion 106 is placed in the annular compartment 104 such that annular gaps are created between the walls of the annular compartment 104 of the delay element 100 and the walls of the tubular protrusion 106. The gaps are filled with a viscous fluid capable of creating a damping shear force when the delay element 100 is moved in relation to the compartment 104, as will be described.

The signal generating element 86 is further arranged with threads 88 along at least a distal part of its outer surface. The threads 88 are arranged to interact with corresponding threads 90 on said actuator, more specifically on a nut 92, which nut 92 is integrally or attached or connected to the actuator 42 by longitudinally extending arms 94. The threads 88 of the signal generating element 86 are further designed as a sort of hex head having six side surfaces as seen in FIG. 4. The hex head threads are arranged to fit into a hex-shaped passage 96 in the hub 98 of the delay element 100, comprised in the signal delay mechanism 84, such that the signal generating element 86 and the delay element 100 are rotationally locked to each other while admitting longitudinal movement between them. The threads 88 on said signal generating element 86 terminate at a certain release point of said signal generating element whereby said signal generating element is released from the actuator and wherein a certain distance D is provided between a distal transversal surface of the signal generating element 86 and the inner transversal surface 15 of the distal housing part 14 at said release point such that the signal generating element 86 is free to be moved in contact with the inner transversal surface 15, thereby generating said audible and/or tactile and/or visual signal.

The activator 74 is preferably a U-shaped bracket having a base 76 and two arms 78, wherein the free ends of the arms 78 are arranged with generally radially outwardly directed ledges 80, and wherein the base is in contact with said signal generating element 86 FIGS. 4 and 5*b*. The arms 78 of the activator 74 are directed in the proximal direction along, and in contact with, the outer surface of the plunger rod 52, and the ledges 80 are arranged to be in contact with a proximally directed surface 82 surrounding the central passage 50 of the actuator 42, FIG. 4*a*.

The drive mechanism further comprises a compression spring 70 which is placed inside a cavity of the plunger rod 52 with a proximal end thereof in contact with an end wall 72 of the plunger rod and a distal end thereof in contact with the base 76 of the U-shaped bracket, FIG. 5*a*.

Thus, the drive mechanism is in the pre-tensioned state when the plunger rod 52 is held in position in relation to the actuator 42 by the protrusions 48 of the arms 46 placed in the cut-outs 54 of the plunger rod 52 such that the compression spring 70 is held tensioned between the end wall 72 of the plunger rod 52 and the base 76 of the activator 74, wherein the arms 46 are prevented from being moved outwardly in the radial direction by the actuator lock sleeve 58 which is positioned radially outside the arms such that the outwardly directed protrusions 56 of the arms are in contact with an inner surface of the actuator lock sleeve 58 and wherein the ledges 80 of the activator 74 are resting on the surface 82 of the actuator 42 such that the activator 74 is prevented from being moved in the distal direction by the force of the spring 70.

Further, the drive mechanism is in the released state when the biased delivery member cover 26 and thereby the actuator lock sleeve 58 are moved longitudinally towards the distal end such that the windows 62 of the actuator lock 58 are placed radially outside the outwardly directed protrusions 56 of the arms 46 of the actuator 42 allowing the arms 46 to flex radially outwards and thereby disengaging from the cut-outs 54 of the plunger rod 52.

The arms 78 of the activator 74 are configured to flex radially inwards such that the ledges 80 are moved out of contact with the surfaces 82 of the actuator 42 when the plunger rod 52 has moved proximally a certain distance and is moved out of contact with the arms 78. The activator 74 is configured to be distally moved by the compression spring 70 when the plunger rod 52 has moved proximally a certain distance and is moved out of contact with the arms 78 such that the activator 74 presses with a distally directed force F on the signal generating element 86. The signal generating element 86 and the delay element 100 are configured to rotate when the activator 74 presses with the distally directed force F on the signal generating element 86.

The device is intended to function as follows. The device is generally delivered to a user with the drive mechanism 40 in the pre-tensioned state, i.e. with compressed compression spring 70 as described above, with the plunger rod 52 held by the actuator 42 as shown in FIG. 5*a*, and with a medicament container 20 placed inside the device. When the device is to be used, the protective cap 16 is removed. The protective cap is preferably arranged with elements that can remove a protective sheath/shield (not shown) surrounding the injection needle 23 when the device is arranged with such a medicament delivery member.

The biased delivery member cover 26 is in an extended proximal position outside the proximal housing part 12 as seen in FIG. 5b by the force of a biased delivery member cover spring 34, thereby hiding the needle 23 from view. The user now places the proximal end of the biased delivery member cover 26 against the dose delivery site and presses the device in the proximal direction. This will cause the biased delivery member cover 26 to slide in the distal direction inside the housing parts of the device, thus causing a penetration of the needle 23 into the skin of the patient, as seen in FIG. 6.

The movement of the biased delivery member cover 26 in the distal direction will cause the elongated arms 30 of the biased delivery member cover 26 to push the actuator lock sleeve 58 in the distal direction due to the contact between the end surfaces 32 of the elongated arms 30 and the proximal end surface 60 of the actuator lock sleeve 58, until the windows 62 of the actuator lock sleeve 58 are placed radially outside the outwardly directed protrusions 56 of the arms 46 of the actuator 42, FIG. 6b. The actuator arms 46 are then free to flex outwards whereby the inwardly directed protrusions 48 of the actuator arms 46 are moved out of contact with the cut-outs 54 of the plunger rod 52.

The plunger rod 52 is now free to move in the proximal direction due to the force of the compression spring 70, wherein the proximal end of the plunger rod 52 acts on, and moves, the stopper 22 inside the medicament container 20 in the proximal direction such that a dose of medicament is expelled through the medicament delivery member 23, as seen in FIG. 7.

When the stopper 23 has been moved by the plunger rod 52 to almost the proximal end inside the medicament container 20, the plunger rod 52 is moved out of contact with the activator 74 as seen in FIG. 7a. The arms 78 of the activator 74 are thus free to flex inwards such that the ledges 80 are moved out of contact with the surfaces 82 of the actuator 42, and due to the compression spring 70, the activator 74 will press with a distally directed force F on the signal generating element 86 of the signal delay mechanism, FIG. 7a. The distal force F will in turn cause the signal generating element 86 to turn/rotate due to the interaction between the threads 88 of the signal generating element 86 and the threads 90 of the nut 92. The turning of the signal generating element 86 will in turn cause the delay element 100 to turn due to the rotational lock between the two via the hex connection. However, since the delay element 100 is in contact with the delaying grease the speed of the turning is slow because of the shear forces in the grease. The dose delivery sequence is now completed.

Figure 8A:
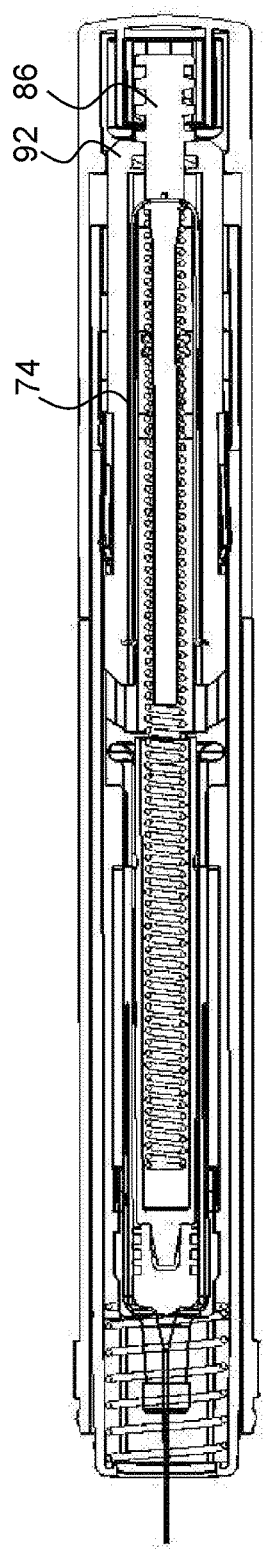
Figure 8B:
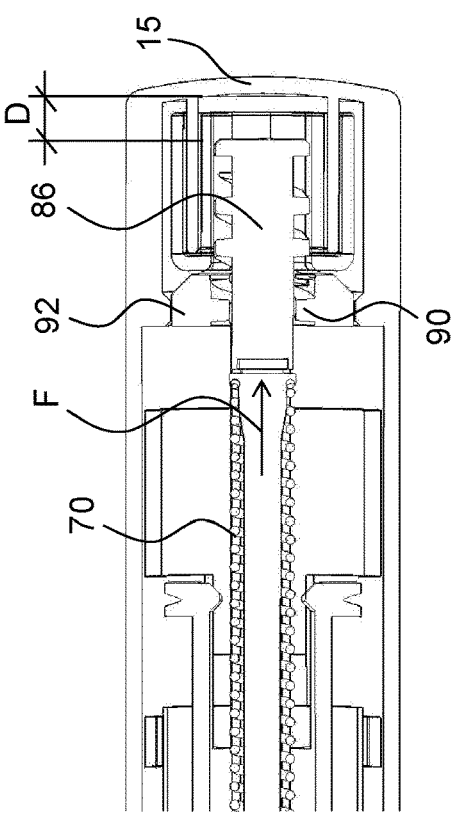

When the signal generating element 86 has turned a predetermined rotational distance, the threads 88 of the signal generating element 86 terminate and the interaction with the threads 90 of the nut 92 is broken. The design is such that there is a distance D between a distal end surface of the signal generating element 86 and a proximally directed surface of the end wall 15 when the threads terminate, as seen in FIG. 8b. The signal generating element 86 is now free to move and will do so because of a remaining force Fr from the compression spring 70. Thus, the signal generating element 86 is urged in the distal direction and will travel the distance D, picking up a certain speed until it hits the distal end wall 15 of the distal housing part. The speed and force of the signal generating element 86 is such that an audible and also tactile signal is generated from the device, which indicates to the user that the injection sequence is completed.

The user can now safely remove the device from the delivery site. The removal will cause the biased delivery member cover 26 to move in the proximal direction due to the force from the biased delivery member cover spring 34, thereby covering the needle 23 as seen in FIG. 11. The elongated arms 30 of the biased delivery member cover 26 will now pass ribs 68 on the inner surface of the distal housing part 14, thereby blocking any subsequent movement of the biased delivery member cover 26 with its elongated arms 30 in the distal direction. The biased delivery member cover 26 is thus locked, preventing any accidental needle sticks. The device may now be discarded.

The signal generating element 86 may have other or additional features for signalling to a user that the medicament delivery sequence is terminated and that it is safe to remove the device. For instance, the distal end of the signal generating element 86 may be arranged with a protrusion 108, FIGS. 11a and b, extending in the distal direction. Further, the distal end wall 15 of the distal housing part is arranged with a passage 110, such that when the signal generating element 86 is released it will hit the end wall 15 as described above, whereby the protrusion 108 will extend through the passage 110. The protrusion 108 preferably has a length such that it will extend a distance from the distally directed surface of the end wall 15. This will enable both a visual and tactile indication that the injection sequence is completed.

It is to be understood that the embodiment described above and shown in the drawings is to be regarded only as a non-limiting embodiment of the invention and that it may be modified in many ways within the scope of the patent claims.

The invention claimed is:

1. A medicament delivery device comprising:
   a housing having a distal and a proximal end, said housing being adapted to receive a medicament container with a delivery member or with a connectable delivery member for delivery of a medicament;
   a drive mechanism having a pre-tensioned state and a released state, where activation of the drive mechanism causes a change from the pre-tensioned state to the released state;
   a biased delivery member cover positioned at least partially and axially movable within the housing, said biased delivery member cover being interactively connected to the drive mechanism such that when said biased delivery member cover is pressed against a delivery site, said drive mechanism is actuated whereby the drive mechanism acts on the medicament container for providing automatic delivery of the medicament; and
   a signal delay mechanism operably connected to said drive mechanism where the signal delay mechanism generates an audible or tactile or visual signal indicating that the medicament has been completely delivered, wherein the signal delay mechanism comprises,
      an activator interactively arranged to said drive mechanism,
      a signal generating element interactively connected to the activator and to an actuator of the drive mechanism, and
      a delay element operably connected to the housing and to the signal generating element for delaying said generation of the audible or tactile or visual signal, where the signal generating element and the delay element are rotationally locked to each other while allowing longitudinal movement between them.

2. Medicament delivery device according to claim 1, wherein the signal generating element is arranged movable in a longitudinal direction in relation to the actuator.

3. Medicament delivery device according to claim 2, wherein the delay element is rotatably connected to the housing and is placed in contact with a viscous media capable of regulating rotational speed of said delay element when the signal generating element acts on the delay element.

4. Medicament delivery device according to claim 3, wherein the signal generating element is arranged with threads configured to cooperate with corresponding fixed threads on said actuator such that said signal generating element and said delay element rotate when said activator is activated.

5. Medicament delivery device according to claim 4, wherein said threads on said signal generating element terminate at a certain release point of said signal generating element whereby said signal generating element is released from the actuator and wherein a certain distance (D) is provided between a distal transversal surface of the signal generating element and an inner transversal surface on the housing at said release point such that said signal generating element is free to be moved in contact with said inner transversal surface, thereby generating said audible or tactile or visual signal.

6. Medicament delivery device according to claim 5, wherein said signal generating element comprises a protrusion extending in a distal direction, and wherein said inner transversal surface on the housing comprises a passage, wherein said protrusion is arranged to extend through said passage for generating the audible or tactile or visual signal.

7. Medicament delivery device according to claim 3, wherein the delay element is a generally tubular body comprising a generally cylindrical hub, wherein an annular compartment is created between said hub and said generally tubular body, and wherein the housing comprises a generally tubular protrusion arranged in said compartment and wherein the viscous media is arranged in said compartment.

8. Medicament delivery device according to claim 7, wherein said viscous media comprises a damping grease.

9. Medicament delivery device according to claim 1, wherein said activator is a U-shaped bracket having a base and two arms, wherein free ends of the arms are arranged with generally radially outwardly directed ledges, and wherein the base is in contact with said signal generating element.

10. Medicament delivery device according to claim 9, wherein the drive mechanism comprises a generally tubular plunger rod partially arranged within a central passage of the actuator and in contact with the arms of the U-shaped bracket such that the ledges are arranged to be in contact with a proximally directed surface surrounding the central passage of the actuator, and a compression spring placed inside a cavity of the plunger rod with a proximal end thereof in contact with an end wall of the plunger rod and a distal end thereof in contact with the base of the U-shaped bracket.

11. Medicament delivery device according to claim 10, wherein the actuator comprises longitudinally extending grooves on which distally directed end surfaces of elongated arms of the biased delivery member cover may slide, and radially flexible and distally directed arms having radially inwardly directed protrusions and outwardly directed protrusions at free ends of the radially flexible and distally directed arms and wherein the radially inwardly directed protrusions are configured to fit into cut-outs of the plunger rod.

12. Medicament delivery device according to claim 11, wherein the drive mechanism further comprises a generally tubularly shaped actuator lock sleeve coaxially and slidably arranged on the actuator and wherein the actuator lock sleeve is further arranged with cut-outs or windows.

13. Medicament delivery device according to claim 12, wherein the drive mechanism is in a pre-tensioned state when the plunger rod is held in position in relation to the actuator by the protrusions of the radially flexible and distally directed arms placed in the cut-outs of the plunger rod such that the compression spring is held tensioned between the end wall of the plunger rod and the base of the activator, wherein the radially flexible and distally directed arms are prevented from being moved outwardly in the radial direction by the actuator lock sleeve which is positioned radially outside the radially flexible and distally directed arms such that the outwardly directed protrusions of the radially flexible and distally directed arms are in contact with an inner surface of the actuator lock sleeve and wherein the ledges of the activator are resting on an inner surface of the actuator such that the activator k prevented from being moved in the distal direction by the force of the spring.

14. Medicament delivery device according to claim 13, wherein the drive mechanism is in a released state when the biased delivery member cover and thereby the actuator lock sleeve are moved longitudinally towards the distal end such that the cut-outs or windows of the actuator lock sleeve are placed radially outside the outwardly directed protrusions of the radially flexible and distally directed arms of the actuator allowing the radially flexible and distally directed arms to flex radially outwards and thereby disengaging from the cut-outs of the plunger rod.

15. Medicament delivery device according to claim 14, wherein the arms of the activator are configured to flex radially inwards such that the ledges are moved out of contact with the inner surface of the actuator when the plunger rod has moved proximally a certain distance and is moved out of contact with the arms of the activator.

16. Medicament delivery device according to claim 14, wherein the activator is configured to be distally moved by the compression spring when the plunger rod has moved proximally a certain distance and is moved out of contact with the arms of the activator such that the activator presses with a distally directed force F on the signal generating element.

17. Medicament delivery device according to claim 16, wherein the signal generating element and the delay element are configured to rotate when the activator presses with the distally directed force F on the signal generating element.

\* \* \* \* \*